United States Patent [19]

Blocker et al.

[11] Patent Number: 4,997,927
[45] Date of Patent: Mar. 5, 1991

[54] IMPROVED PROCESS FOR THE PURIFICATION OF SYNTHETIC OLIGONUCLEOTIDES

[75] Inventors: Helmut Blocker, Hamburg; Ronald Frank, Wolfenbüttel; Gudrun Heisterberg-Moutsis, Heidelberg; Gisela Kurth, Wolfenbüttel; Andreas Meyerhans, Pinneberg, all of Fed. Rep. of Germany

[73] Assignee: Gesellschaft fur Biotechnologishe Forschung mbH (GBF), Braunschweig, Fed. Rep. of Germany

[21] Appl. No.: 770,295

[22] Filed: Aug. 27, 1985

[30] Foreign Application Priority Data

Sep. 13, 1984 [DE] Fed. Rep. of Germany ....... 3433649

[51] Int. Cl.$^5$ .................. C07H 19/00; C07H 21/00
[52] U.S. Cl. ..................................... 536/27; 536/28; 536/29; 536/127
[58] Field of Search ................ 536/27, 28, 29, 127

[56] References Cited

U.S. PATENT DOCUMENTS 4,430,496  2/1984  Abbott ............................. 536/28

FOREIGN PATENT DOCUMENTS 0156414  10/1985  European Pat. Off. ............ 536/27
0174525   3/1986  European Pat. Off. ............ 536/28
0196101  10/1986  European Pat. Off. ............ 536/27
0062199   4/1983  Japan ............................... 536/28
0104399   6/1984  Japan ............................... 536/28
0036493   2/1985  Japan ............................... 536/28
0004174  12/1985  Japan ............................... 536/27
0638599  12/1978  U.S.S.R. ............................ 536/28
1129213  12/1984  U.S.S.R. ............................ 536/28

OTHER PUBLICATIONS

Fieser and Fieser, Reagents for Organic Synthesis, vol. 1, pp. 1255-1256, 1967, J. Wiley and Sons, N.Y.
Handbook of Chemistry and Physics, 60th ed. R. C. Weast and M. J. Astle eds., CRC Press, Boca Raton, FL 1981, p. C-373.
Lehninger, Biochemistry, Worth Publishers Inc., New York, N.Y., 1975, p. 875.

Primary Examiner—John W. Rollins
Assistant Examiner—L. Eric Crane
Attorney, Agent, or Firm—Kane, Dalsimer, Sullivan, Kurucz, Levy, Eisele and Richard

[57] ABSTRACT

A process for the purfication of synthetic oligonucleotides is described which drastically simplifies the hitherto very time consuming purification process. The deprotection solution is adsorbed without being concentrated on a carrier having reversed phase properties and optionally ion exchanger properties, the oligonuleotides without lipophilic protecting group are removed, their protecting group is cleaved off from the adsorbed oligonucleotides, the adsorbed oligonucleotides are washed and eluted from the carrier and then purified in a manner known per se.

20 Claims, 3 Drawing Sheets

FIG.1: scheme of the chemical DNA synthesis on a polymeric carrier

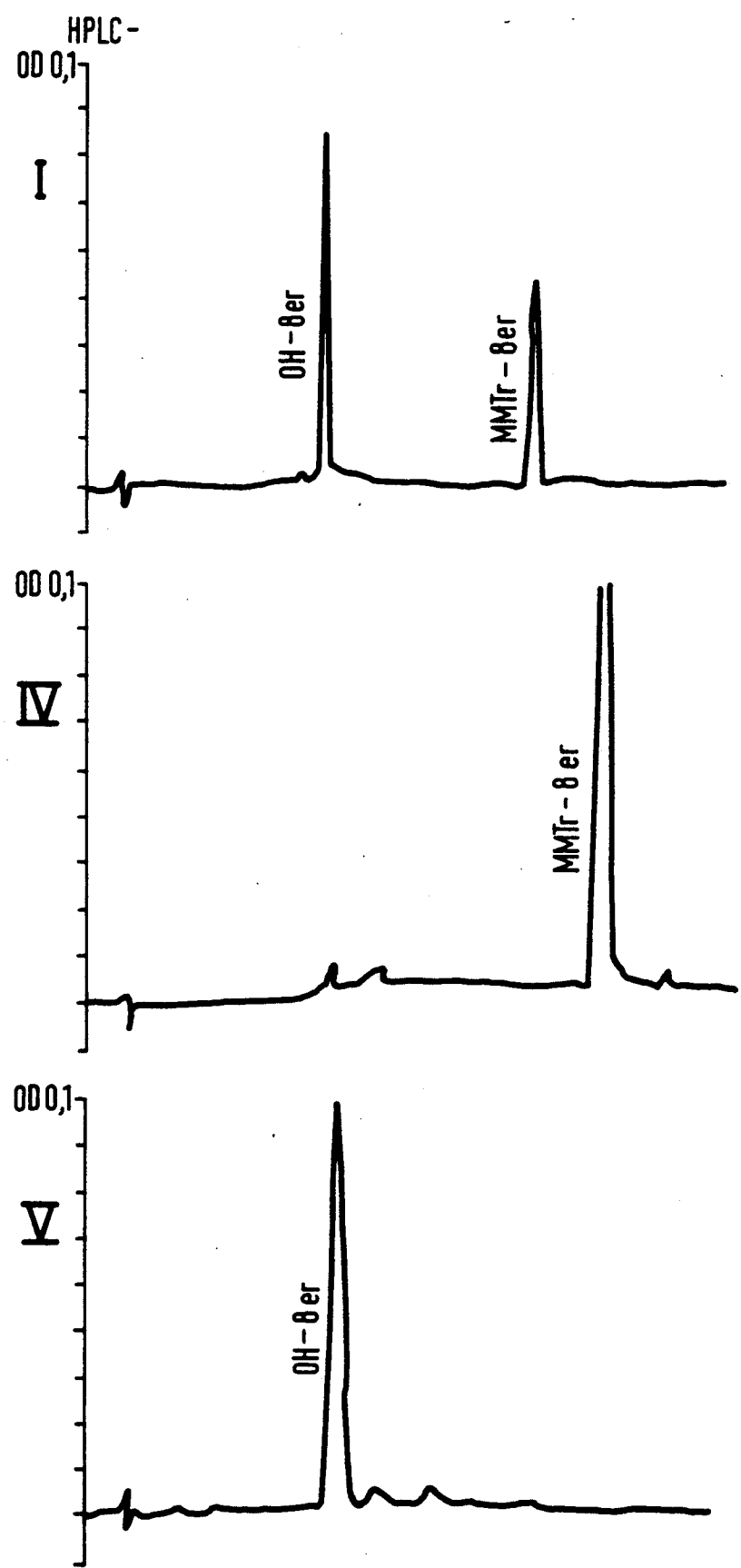

IMPROVED PROCESS FOR THE PURIFICATION OF SYNTHETIC OLIGONUCLEOTIDES

BACKGROUND OF THE INVENTION

1. Field of the Invention

The invention concerns a process for the purification of synthetic oligonucletides which shortens strikingly the purification of synthetic oligonucleotides which is at present very complicated.

2. Brief Description of the Prior Art

By means of the known solid phase methods it is possible to produce a large number of different oligonucleotides relatively quickly.

In the usual processes of the chemical oligonucleotide sythesis (for example on a polymeric carrier, of FIG. 1) 5'-tritylated nucleotide elements are linked step by step in a desired sequence with each other. At the end of such a synthesis different short fragments (interrupted sequences) are obtained apart from the desired completely protected oligonucleotide; these fragments carry either free hydroxyl groups or acetyl groups (truncated by a blocking reaction between the steps of chain extension) or trityl groups at the 5'-terminal in a very limited quantity. Depending on the applied synthesis method (phosphotriester, phosphite triester) different modified oligonucleotides and fragments are also obtained as by-products. However, these products must be subjected to a series of deprotection and purification steps. The time required for this purification is far in excess of the synthesis time.

The following scheme represents the sequence of purification steps which are now-a-days carried out in most of the DNA synthesis laboratories (cf H. G. Gassen and Anne Lang, "Chemical and Enzymatic Synthesis of Gene Fragments, a Laboratory Manual", Verlag Chemie, Weinheim, 1982):

1. partial deprotection and separation from the carrier
2. concentration of the solution
3. chromatographic purification of the tritylated oligonucleotide
4. concentration of the solution
5. acid-catalysed detritylation
6. concentration of the solution
7. high performance liquid chromatography (HPLC) or polyacrylamide gel electrophoresis (PAGE)
8. desalification (desalting) or elution and desalification (desalting)
9. concentration of the solution Of these purification steps steps 2 and 4, i.e. the concentration of the respective solutions, are especially time consuming.

During the deprotection step 1 all protection groups are cleaved off except the lipophilic trityl group. Only the trityl group is to be found at the 5'-terminal of the desired oligonucleotide.

The hydrophobic properties of this trityl group allow a separation from the previously mentioned by-products and cleaved protection groups by means of an interaction with reversed phase material.

SUMMARY OF THE INVENTION

Thus, the invention concerns a process for the purification of synthetic oligonucleotides, which is characterized in that the oligonucleotides (cleaved off from the carrier and still with the lipophilic protecting group) are adsorbed without concentrating the cleaving solution on a carrier with reversed phase properties and optionally ion exchange properties, that the oligonucleotides without any lipophilic protecting group are removed, that the protecting group is cleaved off from the adsorbed oligonucleotides, that the adsorbed oligonucleotides are washed again, that the adsorbed oligonucleotides are eluted from the carrier and that the eluted oligonucleotides are then further purified in a manner known per se.

BRIEF DESCRIPTION OF THE DRAWINGS

FIG. 3 shows HPLC diagrams of a mixture of the compounds I, IV and V as described more fully hereinafter.

DETAILED DESCRIPTION OF THE PREFERRED EMBODIMENTS OF THE INVENTION

For the first time, the combination of a hydrophobic adsorption material with reversed phase properties and of an ion exchanger according to the invention allows the following steps to be carried out in combination as a chromatographic type operation:

a direct adsorption of the oligonucleotide (protected by a lipophilic protecting group) from a deprotection solution purification of the lipophilic protected oligonucleotide cleaving off of the lipophilic protecting group from the adsorbed compound.

According to the process of the invention steps 2 to 5 of the above mentioned scheme are combined in a chromatographic operation.

According to a preferred embodiment of the process of the invention the ammoniacal cleavage solution from step 1 is put on a column after evaporation of the ammonium, the column being packed with polytetrafluoroethylene (PTFE, of Römpps Chemie-Lexikon, edition 7, page 3478 (1977)) and DEAE-cellulose (cf Römpps Chemie-Lexikon, edition 8, page 629 and 874 (1981)) where the polytetrafluoroethylene and the DEAE-cellulose are mixed intimately with each other.

The oligonucleotide present in the solution and trity-lated at the 5'-terminal is adsorbed onto the solid phase. A large amount of protection groups and, in addition, present oligonucleotides without any trityl group are removed in a separation step preferably with a triethyl ammonium hydrogen carbonate solution (step 3 of the above mentioned scheme). Then the trityl group is cleaved off by treating with an acid, preferably with dichloroacetic acid in dichloromethane (step 5 of the scheme). The completely deprotected oligonucleotide is now eluted from the adsorption material after a further washing step. Now the prepurified oligonucleotide can be isolated more simply in homogenous form by other purification methods (e.g. ion exchange, electrophoresis; step 7 of the scheme).

In the process according to the invention for the purification of synthetic oligonucleotides different solutions are passed through a suitable adsorption material. Therefore, both a manual operation and an automatic operation are possible. Such a purification apparatus could be coupled with DNA synthesis devices on-line.

The purification process of the invention is substantiated by an example of a sample mixture (I) of 5'-hydroxyoctanucleotide (II) and purified 5'-tritylated octanucleotide (III).

Figure 1:
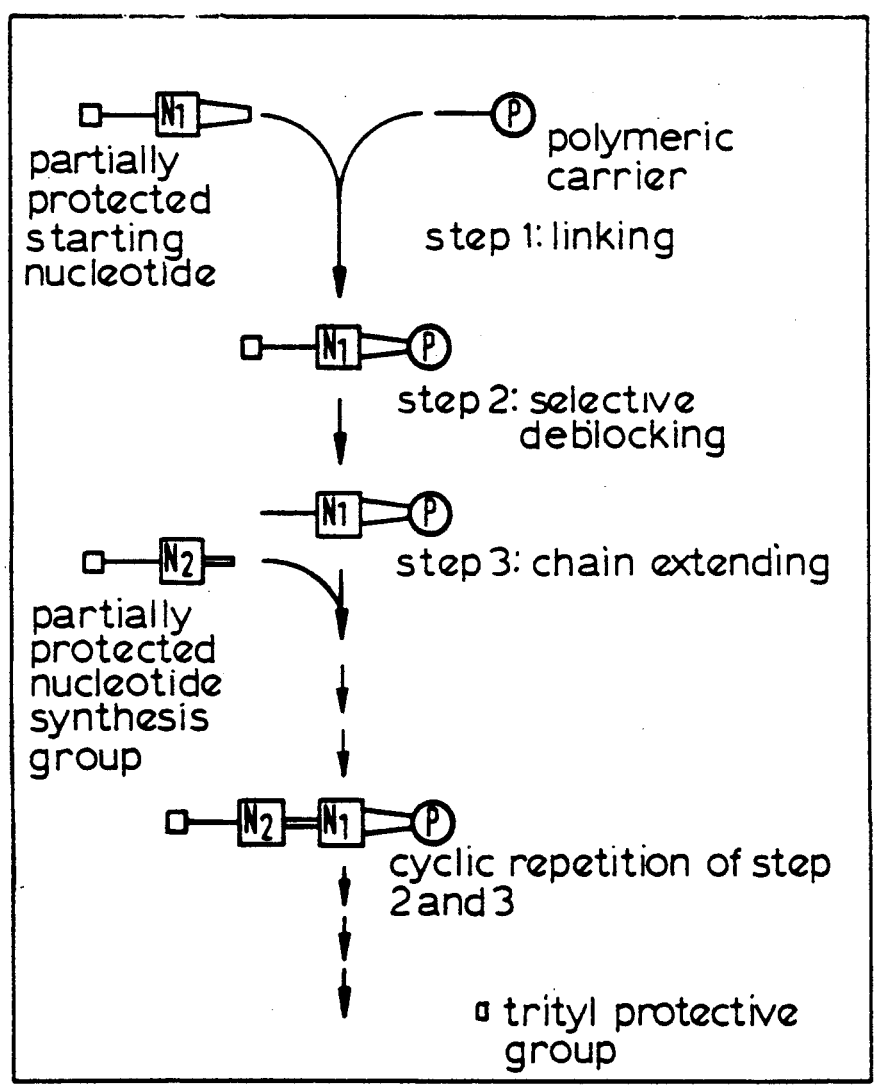
FIG. 1 is a flow diagram showing an embodiment process of the invention.
Figure 2:
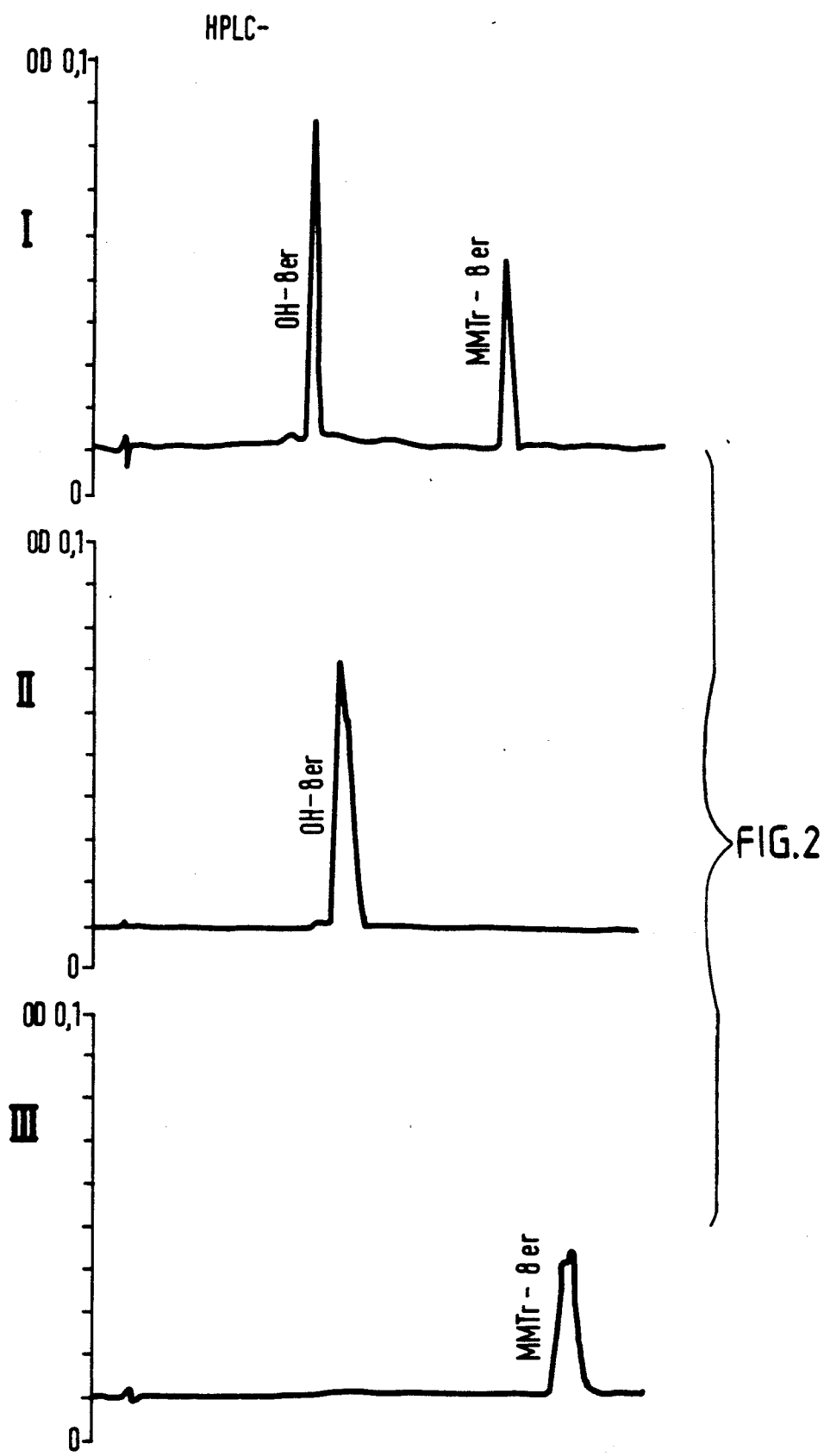
FIG. 2 shows high pressure liquid chromatography (HPLC) diagrams showing quantitative detritylation in the process of the invention.

FIG. 2 shows the respective HPLC diagrams.

The quantitative detritylation is substantiated using 5'-tritylated octanucleotide as example.

FIG. 3 shows the HPLC diagrams of the mixture (I), the 5'-tritylated octanucleotide (IV) and the hydroxyoctanucleotide (V).

The following experiments explain the invention.

Adjuvants and Chemicals disposable filter columns with double 20 μm frit 6 ml article No. 71216 (Baker)
adaptor for 6 ml filter columns article No. 71220 (Baker)
connection for pressurized air
filter column packing: polytetrafluoroethylene=PTFE (ICI)
DEAE-cellulose DE 52 preswollen, catalogue No. 4057-050 (Whatman)
solvents:
  2M triethylammonium hydrogen carbonate (pH 7.5)
  2M TEAB (2 mol/l TEAB)
  ethanol absolute
  dichloromethane=$CH_2Cl_2$
  3% dichloroacetic acid in dichloromethane=DCA

Packing of Filter Columns 1200 mg PTFE
200 mg DEAE-cellulose
mix in dry state
pack between the two frits of the filter column
press the material down by pressure on the upper frit
all solutions are forced with compressed air through the column material

Washing and Equilibrating the Column 2 ml ethanol
2 ml 100 mM (100 mmol/l) TEAB
2 ml 2M TEAB/ethanol (4:1)
2 ml 50 mM TEAB

Feeding the Column

The packed carrier material of a 0.5 μmol oligonucleotide synthesis charge (phosphotriester method) is given into 4 ml $NH_3$ (33%)/pyridine (9:1) and left at room temperature for two days and at 50° C. for 12 h in a closed vessel. The vessel is opened and the ammonia is evaporated at 50° C. in a sand bath (about 2 h). The remaining solution is pipetted off and the carrier material washed with 2 ml 50 mM TEAB and with 2 ml 50 mM TEAB/ethanol (1:1). The three solutions are put together and fed onto the column.

First Washing Step

3 × 2 ml 50 mM TEAB
2 ml 100 mM TEAB
Separation (elution of non-tritylated components)

2 × 2 ml 2 M TEAB/ethanol (95:5)

Second Washing Step 2 ml 50 mM TEAB
2 ml ethanol
2 ml $CH_2Cl_2$

Acid Treatment

3% dichloroacetic acid in dichloromethane is forced through for 3 min; then rinsing with
2 ml $CH_2Cl_2$
2 ml ethanol
2 ml 50 mM TEAB

Eluation

2×2 ml 2M TEAB/ethanol (4:1)

Concentration

The eluate (4 ml) is concentrated in a vacuum up to dryness. Then the residue is further purified according to step 7 of the above described scheme.

Explanation of the HPLC Diagrams

The separation according to the invention is substantiated by means of an example of a mixture of purified 5'-tritylated octanucleotide and 5'-hydroxyoctanucleotide; HPLC diagrams I, II and III.

Separation of the Substances on a $C_{18}$-silica gel column (Nucleosil RPC18 column) 0.4×25 cm (Macherey-Nagel)
flow rate: 2 ml/min
gradient of 5% to 50% acetonitrile in 0.1M triethylammonium acetate (pH 6.3).

Quantitative Detritylation exemplified by 5'-tritylated octanucleotide; HPLC diagrams I, IV and V.

Separation of the Substances on a RPC18 column (cf above).

EXAMPLE

The oligonucleotide GTT GTT TAA TGG GTA AAC is synthesized on a cellulose filter by the phosphotriester method. The elements are dimethoxy-tritylated base protected phosphodiesters (cf R. Frank, W. Heikens, G. Heisterberg-Moutsis and H. Blöcker, Nucleic Acids Research, volume 11, page 4365 (1983)).

The cellulose filter charged with 0.5 μmol 18-mer is given into 4 ml $NH_3$ (33%)/pyridine (9:1) and left at room temperature for 2 days and at 50° C. for 12 h in a closed vessel. The vessel is opened and the ammonia is evaporated at 50° C. in a sand bath (about 2 h). The remaining solution is pipetted off and the cellulose filter is washed with 2 ml 50 mM TEAB and 2 ml 50 mM TEAB/ethanol (1:1). The three solutions are collected and put onto the column; the column is washed three times with 2 ml 50 mM TEAB and once with 2 ml 100 mM TEAB. The non-tritylated component is separated by rinsing the column twice with 2 ml 2M TEAB/ethanol (95:5). The column is rinsed with 2 ml 50 mM TEAB, 2 ml ethanol and 2 ml dichloromethane. 3% dichloroacetic acid in dichloromethane is forced through the column for 3 min; then the column is rinsed with 2 ml dichloromethane, 2 ml ethanol and 2 ml 50 mM TEAB. The column is eluted twice with 2 ml 2M TEAB/ethanol (4:1). The eluate (4 ml) is concentrated to dryness in a vacuum. The residue is further purified by ion exchange HPLC chromatography and desalification desalting (step 7 of the above mentioned scheme). Finally, the purified 18-mer is obtained.

We claim:

1. Process for the purification of a synthetic oligonucleotide, which consists essentially of;
   providing the synthesized oligonucleotide in an aqueous cleaving solution as obtained after being cleaved off from a support carrier used in the synthesis and having a lipophilic protecting group;
   adsorbing on a reverse phase support carrier, the provided oligonucleotide;
   removing contaminant oligonucleotides lacking a lipophilic protecting group;
   removing the lipophilic protecting group from the adsorbed oligonucleotide;
   washing the adsorbed oligonucleotide; and
   eluting the washed adsorbed oligonucleotide from the support carrier.

2. Process according to claim 1 wherein polytetrafluoroethylene is used as the reverse phase support carrier.

3. Process according to claim 1 wherein the aqueous cleaving solution is adsorbed on the reverse phase support carrier after the evaporation of ammonia.

4. Process according to claim 1 wherein the cleaving solution is put onto a column filled with the carrier and washed with a buffer solution, treated with an acid, washed and eluted from the carrier with a buffer solution and an organic water-miscible solvent.

5. Process according to claim 4, wherein triethyl ammonium hydrogen carbonate solution is used as the buffer solution.

6. Process according to claim 4, wherein dichloroacetic acid in dichloromethane is used as the acid.

7. Process according to claim 1, wherein the elution is carried out with triethyl ammonium hydrogen carbonate and ethanol at a ratio of 4:1.

8. A process for the purification of a synthetic oligonucleotide, which consists essentially of;
   providing the oligonucleotide having a lipophilic protecting group in admixture with a contaminant oligonucleo-tide lacking a lipophilic protecting group;
   absorbing on a carrier selected from the group consisting of a reverse phase carrier and a carrier with reversed phase and ion-exchange properties, the provided oligonucleotide;
   removing the contaminant oligonucleotides lacking a lipophilic protecting group;
   cleaving off the lipophilic protecting group from the adsorbed oligonucleotide;
   washing the adsorbed oligonucleotide; and
   eluting the washed adsorbed oligonucleotide from the carrier.

9. Process for the purification of a synthetic oligonucleotide, which consists essentially of;
   providing the oligonucleotide in an aqueous cleaving solution as cleaved off from a carrier and having a lipophilic protecting group;
   absorbing on a carrier with reversed phase properties and ion exchange properties, the provided oligonucleotide;
   removing contaminant oligonucleotides lacking a lipophilic protecting group;
   cleaving off the lipophilic protecting group from the adsorbed oligonucleotide;
   washing the adsorbed oligonucleotide; and
   eluting the washed adsorbed oligonucleotide from the carrier.

10. Process according to claim 9, wherein polytetrafluoroethylene is used as the carrier.

11. Process according to claim 9 wherein polytetrafluoroethylene and DEAE-cellulose in combination is used as the carrier.

12. Process according to claim 9 wherein the aqueous cleaving solution is adsorbed on the carrier after the evaporation of ammonia.

13. Process according to claim 9 wherein the cleaving solution is put onto a column filled with the carrier and washed with a buffer solution, treated with an acid, washed and eluted from the carrier with a buffer solution and an organic water-miscible solvent.

14. Process according to claim 13 wherein triethyl ammonium hydrogen carbonate solution is used as the buffer solution.

15. Process according to claim 13 wherein dichloroacetic acid in dichloromethane is used as the acid.

16. Process according to claim 9, wherein a compound selected from the group consisting of ethanol and dichloromethane is used as the wash, after acid treatment.

17. Process according to claim 9 wherein the elution is carried out with triethyl ammonium hydrogen carbonate and ethanol at a ratio of 4:1.

18. Process according to claim 9 wherein the cleaving solution in which the oligonucleotide is provided is not concentrated.

19. Process according to claim 16 wherein the compound selected is ethanol.

20. Process according to claim 16 wherein the compound selected is dichloromethane.

* * * * *

UNITED STATES PATENT AND TRADEMARK OFFICE
CERTIFICATE OF CORRECTION

PATENT NO. : 4,997,927
DATED : March 5, 1991
INVENTOR(S) : Helmut Blocker et al

It is certified that error appears in the above-identified patent and that said Letters Patent is hereby corrected as shown below:

Col. 1, line 17; "sythesis" should read -- synthesis -- .

Col. 1, line 20; "interrupted" should read -- truncated -- .

Col. 1, line 24; "truncated" should read -- introduced -- .

Col. 6, Claim 21 has been omitted from the issued patent please insert after line 54:

-- Claim 21. Process according to claim 1 wherein dichloromethane is used as the wash, after acid treatment. --

Signed and Sealed this

Eleventh Day of August, 1992

*Attest:*

DOUGLAS B. COMER

*Attesting Officer*   *Acting Commissioner of Patents and Trademarks*